United States Patent [19]
Thompson et al.

[11] Patent Number: 5,368,926
[45] Date of Patent: Nov. 29, 1994

[54] FLUID ACCEPTING, TRANSPORTING, AND RETAINING STRUCTURE

[75] Inventors: Hugh A. Thompson, Fairfield; Tracey A. Martin, Cincinnati; Thomas A. Inglin, Hamilton, all of Ohio

[73] Assignee: The Procter & Gamble Company, Cincinnati, Ohio

[21] Appl. No.: 943,261

[22] Filed: Sep. 10, 1992

[51] Int. Cl.⁵ .............................................. B32B 5/06
[52] U.S. Cl. ................................. 428/284; 428/297; 428/298; 428/913
[58] Field of Search ............... 428/284, 913, 297, 298; 604/358, 367

[56] References Cited

U.S. PATENT DOCUMENTS

| | | | |
|---|---|---|---|
| Re. 32,741 | 8/1988 | Miyoshi et al. | 528/295 |
| 3,121,040 | 2/1964 | Shaw et al. | 161/177 |
| 3,156,607 | 11/1964 | Strachan | 161/177 |
| 3,194,002 | 7/1965 | Raynolds et al. | 57/140 |
| 3,272,901 | 9/1966 | Sims | 264/177 |
| 3,295,308 | 1/1967 | Raynolds et al. | 428/397 |
| 3,340,571 | 9/1967 | Bishop et al. | 18/8 |
| 3,383,276 | 5/1968 | Gould | 161/177 |
| 3,508,390 | 4/1970 | Bagnall et al. | 57/140 |
| 3,538,208 | 11/1970 | Ohtsuka | 264/89 |
| 3,613,778 | 10/1971 | Feldman, Jr. | 165/105 |
| 3,633,538 | 1/1972 | Hoeflin | 118/76 |
| 3,700,545 | 10/1972 | Matsui et al. | 161/175 |
| 4,054,709 | 10/1977 | Belitsin et al. | 428/224 |
| 4,179,259 | 12/1979 | Belitsin et al. | 428/461 |
| 4,364,998 | 12/1982 | Wei | 428/399 |
| 4,381,325 | 4/1983 | Masuda et al. | 428/91 |
| 4,405,686 | 9/1983 | Kuroda et al. | 428/374 |
| 4,492,731 | 1/1985 | Bankar et al. | 428/362 |
| 4,622,054 | 11/1986 | Huey et al. | 65/2 |
| 4,636,234 | 1/1987 | Huey et al. | 65/2 |
| 4,668,566 | 5/1987 | Braun | 428/286 |
| 4,707,409 | 11/1987 | Phillips | 428/397 |
| 4,710,185 | 12/1987 | Sneyd, Jr. et al. | 604/372 |
| 4,713,289 | 12/1987 | Shiffler | 428/361 |
| 4,812,361 | 3/1989 | Takemoto et al. | 428/397 |
| 4,842,792 | 6/1989 | Bagrodia et al. | 264/130 |
| 5,057,368 | 10/1991 | Largman et al. | 428/397 |
| 5,200,248 | 4/1993 | Thompson et al. | 428/131 |

FOREIGN PATENT DOCUMENTS

| | | |
|---|---|---|
| 0233702 | 8/1987 | European Pat. Off. . |
| 0301874A1 | 2/1989 | European Pat. Off. . |
| 0391814A2 | 10/1990 | European Pat. Off. . |
| 0493728A1 | 12/1991 | European Pat. Off. . |
| 955625 | 1/1950 | France . |
| 7523149 | 2/1975 | Japan . |
| 3152449A | 8/1979 | Japan . |
| 7001005B | 8/1979 | Japan . |
| 151617 | 11/1979 | Japan . |
| 8018430A | 2/1983 | Japan . |
| 1075844A | 9/1984 | Japan . |
| 1083313A | 9/1984 | Japan . |
| 2006933A | 7/1985 | Japan . |
| 2015324A | 7/1985 | Japan . |
| 2028405A | 8/1985 | Japan . |
| 2170510A | 1/1986 | Japan . |
| 2215028A | 3/1986 | Japan . |
| 2238817A | 4/1986 | Japan . |
| 2238818A | 4/1986 | Japan . |
| 2238833A | 4/1986 | Japan . |
| 2238842A | 12/1986 | Japan . |
| 1026715A | 2/1988 | Japan . |
| 1162813A | 6/1989 | Japan . |
| 1488676 | 10/1977 | United Kingdom . |
| WO93/01780 | 2/1943 | WIPO ................ A61F 13/15 |

OTHER PUBLICATIONS

"The Fundamentals of Fiber Formation", Andrzej Ziabicki, Wiley–Interscience Publication (New York, 1976), pp. 360–366.
"Man–Made Fibers—Science and Technology", H. F. Mark, et al., vol. I, pp. 227–231, Interscience Publishers, John Wiley & Sons, Inc., 1967.

*Primary Examiner*—James J. Bell
*Attorney, Agent, or Firm*—Kevin C. Johnson; E. K. Linman

[57] ABSTRACT

The present invention provides a fluid accepting, transporting and retaining structure, useful in disposable absorbent articles. In-use fluid deposited on a disposable absorbent article employing such a structure is moved via interfiber and intrafiber transport to a fluid retention area remote from the point of fluid insult. By moving fluid away from the point of insult a more effective use of the absorbent core is achieved providing a clean and dry surface for the wearer.

9 Claims, 5 Drawing Sheets

FLUID ACCEPTING, TRANSPORTING, AND RETAINING STRUCTURE

FIELD OF THE INVENTION

The present invention relates to fluid accepting, transporting, and retaining structures, and more specifically, to nonwoven webs capable of both intrafiber and interfiber fluid transport.

BACKGROUND OF THE INVENTION

A wide variety of structures for disposable absorbent articles to collect body fluids are known in the art. Commercial absorbent articles include diapers, adult incontinence products, catamenials and bandages. Disposable products of this type comprise some functional members for accepting, transporting and retaining fluids. Generally, such absorbent articles contain a core of absorbent materials mainly comprising fibrous cellulose. Typically, such articles include a fluid-permeable topsheet, an absorbent core and a fluid-impermeable backsheet.

In the case of disposable absorbent articles, the users have come to expect a high level of performance in terms of comfort and fit, retention of fluid, and minimal leakage. Above all, leakage of fluid from the absorbent article is regarded as totally unacceptable.

When nonwoven webs are employed in disposable absorbent articles, the simple ability to absorb a liquid is generally not sufficient to ensure optimum performance in a product. For example, during use, many absorbent articles experience multiple insults of a liquid. In order to ensure proper absorption of subsequent insults, it is generally desired that the first insult of liquid be not only absorbed but also transported within the absorbent article to areas where the liquid is to be retained, preferably, remote from the point of insult.

When nonwoven webs are employed in an absorbent article, it is desirable to put the nonwoven web into contact with a fluid storage material. Such fluid storage materials are known to those skilled in the art and are generally capable of absorbing several times their weight in liquid and holding it against capillary suction. If the nonwoven web contacting the storage material is not able to transport a liquid from the point of liquid insult, all of the storage material must be placed in the general area where the insult occurs. However, this is not a ways desirable.

Specifically, fluid is usually applied to disposable absorbent articles near their central portion. If all of the liquid storage material must be placed in the central portion of the product, the product becomes uncomfortable and product design options are thus limited. Therefore, it is desirable to more evenly distribute the fluid storage material throughout the product.

When nonwoven webs are employed in absorbent products, it is desirable that the web be able to quickly accept a liquid. However, simultaneous liquid transport and rapid acceptance has been difficult to achieve.

SUMMARY OF THE INVENTION

The present invention pertains, in a preferred embodiment, to a structure for accepting, transporting, and retaining fluids. The structure includes a nonwoven comprising a plurality of hydrophilic capillary channel fibers capable of interfiber and intrafiber fluid acceptance and transport. The fi bets have at least one capillary channel formed from a base and two substantially parallel walls extending from the base. A high-suction absorbent core is in fluid communication with the nonwoven.

Preferably, the divergence of the substantially parallel walls of the capillary channel fibers of the nonwoven is less than about 40°. Preferably, the slenderness ratio of the capillary channel fibers forming the nonwoven is at least about 9. The capillary suction of the absorbent core is preferably at least about 6 cm. Preferably, the capillary channel width of the capillary channel fibers of said nonwoven is from about 10 microns to about 200 microns. The denier of the capillary channel fibers of said nonwoven is preferably greater than about 5.

Preferably, the structure includes a first nonwoven comprising a plurality of hydrophilic capillary channel fibers capable of interfiber and intrafiber fluid acceptance and transport. The fibers have at least one capillary channel formed from a base and two substantially parallel walls extending from the base. Preferably, the structure includes a second nonwoven superposed upon the first nonwoven and a high-suction absorbent core in fluid communication with the nonwovens.

Preferably, the second nonwoven comprises a plurality of hydrophilic capillary channel fibers capable of interfiber and intrafiber fluid acceptance and transport. The fibers have at least one capillary channel formed from a base and two substantially parallel walls extending from the base.

In another preferred embodiment, the present invention also pertains to an absorbent article. The absorbent article includes a fluid pervious topsheet and a fluid impervious backsheet joined to the topsheet. A high-suction absorbent core is positioned between the topsheet and the backsheet. The core has an uppermost surface facing the topsheet and a lowermost surface facing the backsheet. A nonwoven is positioned between the topsheet and the absorbent core. The nonwoven comprises a plurality of hydrophilic capillary channel fibers capable of intrafiber and interfiber fluid acceptance and transport. The fibers have at least one capillary channel formed from a based and two substantially parallel walls extending from the base.

In another preferred embodiment, the present invention also pertains to an absorbent article. The absorbent article includes a fluid pervious topsheet. The topsheet comprises a nonwoven comprised of a plurality of hydrophilic capillary channel fibers capable of intrafiber and interfiber fluid acceptance and transport. The fibers having at least one capillary channel formed from a base and two substantially parallel walls extending from the base. A fluid impervious backsheet is joined to the topsheet. A high-suction absorbent core is positioned between the topsheet and the backsheet. The core has an uppermost surface facing the topsheet and a lowermost surface facing the backsheet.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify identical elements and wherein;

DETAILED DESCRIPTION OF THE INVENTION

1. General Description of the Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
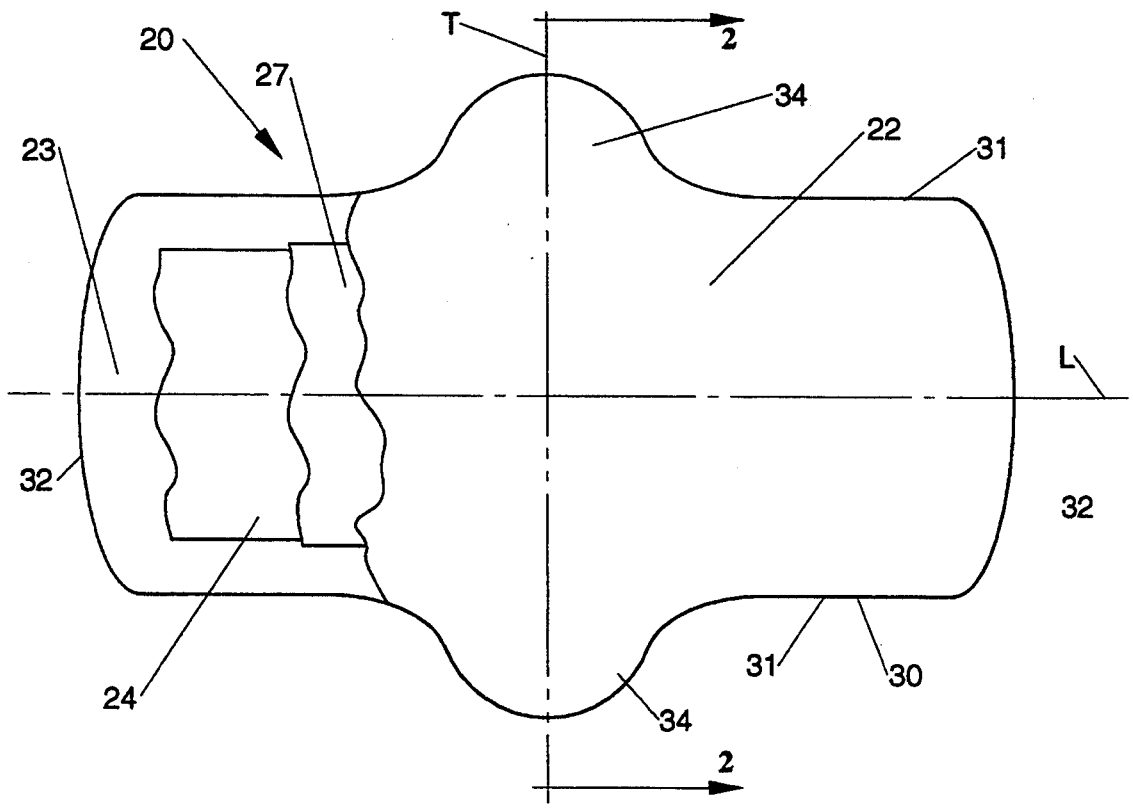
FIG. 1 is a top plan view of a preferred sanitary napkin of the present invention with portions cut-away to more clearly show the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the structure being cut-away to more clearly show the construction of the sanitary napkin 20 and with the portion of the sanitary napkin 20 which faces or contacts the wearer 20a, oriented towards the viewer. As shown in FIG. 1, the sanitary napkin 20 preferably comprises a liquid pervious topsheet 22, a liquid impervious backsheet 23 joined with the topsheet 22, an absorbent core 24 positioned between the topsheet 22 and the backsheet 23, and a fluid accepting and transporting layer 27 positioned between the topsheet 22 and the absorbent core 24.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
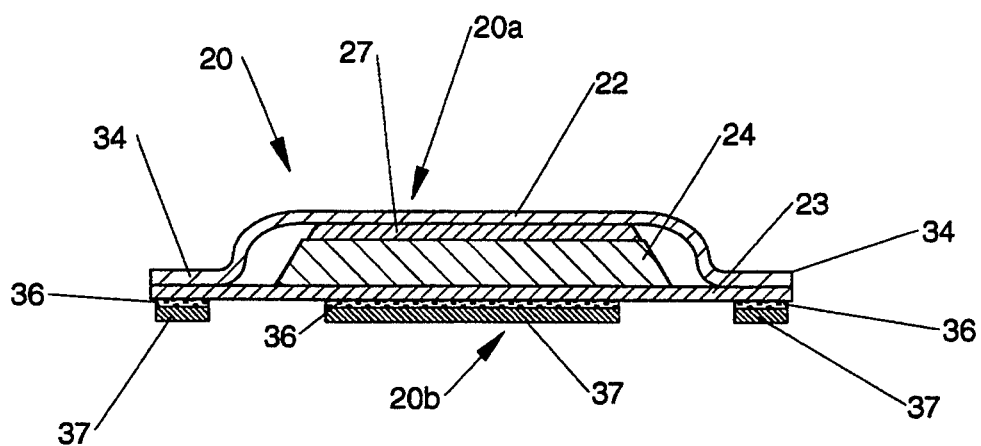
FIG. 2 is a cross-sectional view of the sanitary napkin of FIG. 1 taken along line 2—2.

FIG. 2 is a cross-sectional view of the sanitary napkin 20 taken along section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

Figure 3:
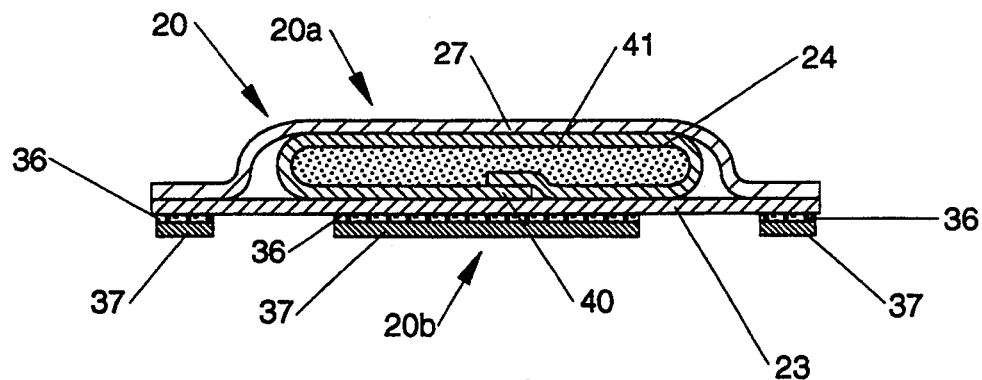
FIG. 3 is a cross-sectional view of another embodiment of a sanitary napkin of the present invention.

FIG. 3 is a cross-sectional view of another embodiment of a sanitary napkin 20 of the present invention. As can be seen in FIG. 3, the sanitary napkin 20 preferably comprises a fluid accepting and transporting layer 27, a liquid impervious backsheet 23 joined with the fluid accepting and transporting layer 27, and an absorbent core 24 positioned between the fluid accepting and transporting layer 27 and the backsheet 23.

Figure 4:
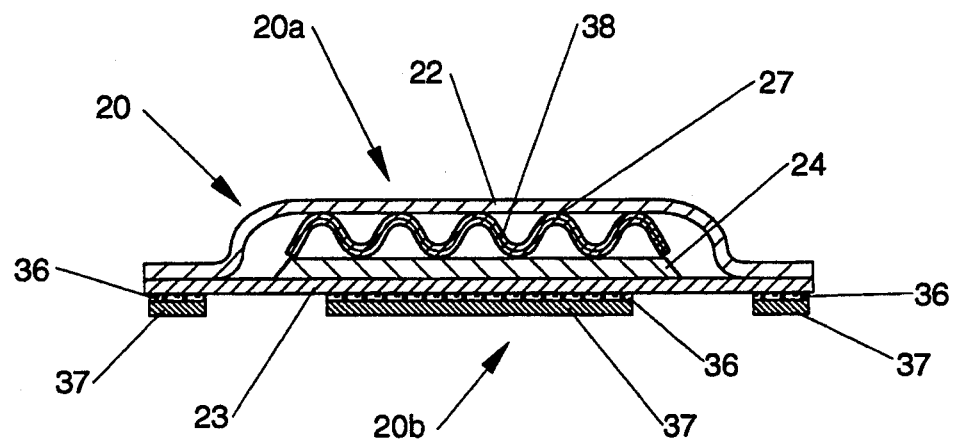
FIG. 4 is a cross-sectional view of another embodiment of a sanitary napkin of the present invention.

FIG. 4 is a cross-sectional view of another embodiment of a sanitary napkin 20 of the present invention. As can be seen in FIG. 4, the sanitary napkin 20 preferably comprises a liquid pervious topsheet 22, a liquid impervious backsheet 23 joined with the topsheet 22, an absorbent core 24 positioned between the topsheet 22 and the backsheet 23, a pleated fluid accepting and transporting layer 27 positioned between the topsheet 22 and the absorbent core 24, and a pleated tissue 38 positioned between the fluid accepting and transporting layer 27 and the absorbent core 24. Preferably, the pleated tissue 38 has a basis weight of from about 0.025 g/in$^2$ to about 0.045 g/in$^2$ and a density of from about 0.06 to about 0.11 g/cm$^3$. Exemplary tissues are manufactured by the Fort Howard Corporation, Green Bay, Wis.

Figure 5:
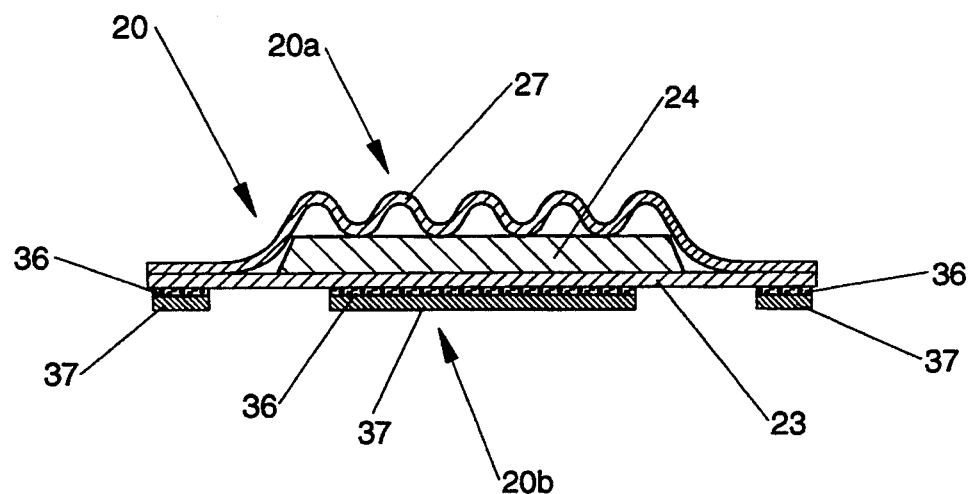
FIG. 5 is a cross-sectional view of another embodiment of a sanitary napkin of the present invention.
Figure 6:
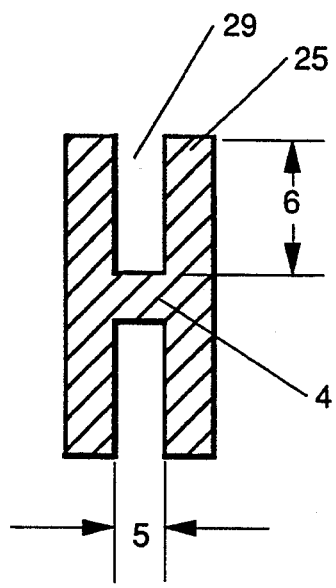
FIG. 6 is a cross-section view of a symmetrical "H"-shaped capillary channel fiber with a flat base (4), width between walls (5), and depth-of-walls (6)
Figure 7:
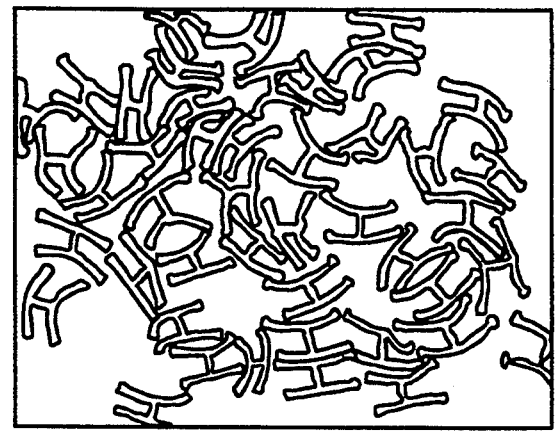
FIG. 7 is an illustration of a capillary channel fiber cross-section.
Figure 8:
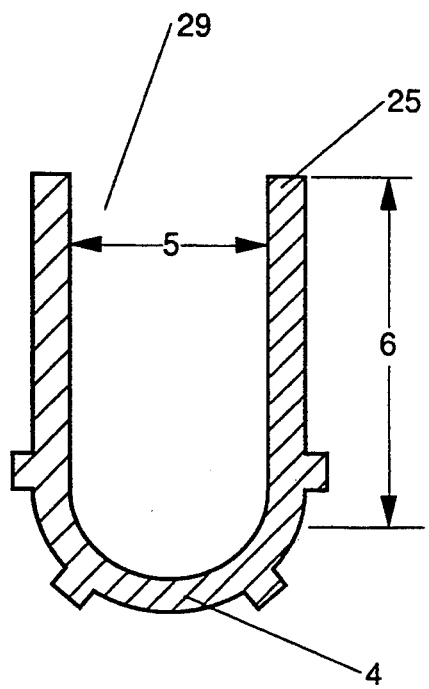
FIG. 8 is a cross-section view of a symmetrical "U"-shaped capillary channel fiber with a curved base (4), width between walls (5), and depth-of-walls (6)
Figure 9:
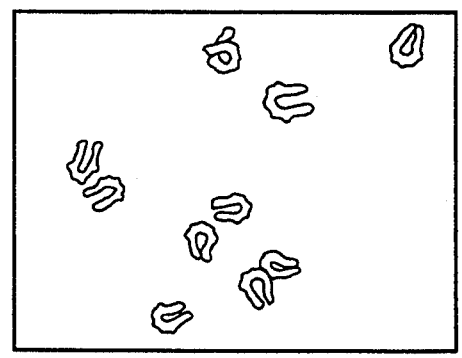
FIG. 9 is an illustration of a capillary channel fiber cross-section.

FIG. 5 is a cross-sectional view of another embodiment of a sanitary napkin 20 of the present invention. As can be seen in FIG. 5, the sanitary napkin 20 preferably comprises a pleated fluid accepting and transporting layer 27, a liquid impervious backsheet 23 joined with the pleated fluid accepting and transporting layer 27, and an absorbent core 24 positioned between the pleated fluid accepting and transporting layer 27 and the absorbent core 24.

In addition to having a longitudinal direction and a transverse direction, the sanitary napkin 20 also a "z" direction or axis, which is the direction proceeding down through the body-contacting layer, e.g., topsheet 22 or fluid accepting and transporting layer 27, and into whatever fluid storage means, e.g., absorbent core 24, that may be provided. The objective is to provide a gradient of capillary suction between the body-contacting layer and the underlying layer or layers of the articles herein, such that fluid is eventually drawn in the "z" direction and away from the body-contacting layer of the article into its ultimate storage layer.

By employing a fluid accepting and transporting layer preferably comprised of a plurality of fibers having external capillary channels, fluid is transported from the point of insult to areas where the liquid is to be retained which enhances the overall useful absorbency of the article.

The individual components of the sanitary napkin will now be looked at in greater detail.

2. Individual Components of the Sanitary Napkin

A. The Topsheet

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet 22 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; U.S. Pat. No. 4,629,643 issued to Curro et al. on Dec. 16, 1986; and U.S. Pat. No. 5,006,394 issued to Baird on Apr. 9, 1991. Each of these patents are Incorporated herein by reference. The preferred topsheet 22 for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet 22 is hydrophilic so as to help liquid transfer through the topsheet 22 faster than if the body surface was not hydrophilic. This will diminish the likelihood that menstrual fluid will flow off the topsheet 22 rather than flowing into and being absorbed by the absorbent core 24. In a preferred embodiment, surfactant is incorporated into the polymeric materials of the formed film topsheet 22 such as is described in U.S. patent application Ser. No. 07/794,745 entitled "Absorbent Article Having A Nonwoven and Apertured Film Coversheet" filed on Nov. 19, 1991 by Aziz et al. Alternatively, the body surface of the topsheet 22 can be made hydrophilic by treating it with a surfactant such as is described in U.S. Pat. No. 4,950,264 issued to Osborn on Aug. 21, 1991 and U.S. Pat. No. 5,009,653 issued to Osborn on Apr. 23, 1991 both of which are incorporated herein by reference.

In an alternative embodiment illustrated in FIGS. 3 and 5 the fluid accepting and transporting layer 27 is used as a topsheet for the sanitary napkin 20. The structure of the fluid accepting and transporting layer 27 will be described in greater detail herein below.

B. The Absorbent Core

The absorbent core 24 may be any absorbent means which is capable of absorbing and retaining liquids (e.g., menses and/or urine) against capillary suction. As shown in FIGS. 1 and 2, the absorbent core 24 has a body surface, a garment surface, side edges, and end edges. The absorbent core 24 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these provided they absorb and retain liquids against capillary suction.

The configuration and construction of the absorbent core 24 may also be varied (e.g., the absorbent core may have varying caliper zones, or may have profiling so as to be thicker in the center), hydrophilic gradients, superabsorbent gradients, or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; U.S. Pat. No. 5,009,653 issued to Osborne on Apr. 23, 1991; and European Patent Application No. 0 198 683, The Procter & Gamble Company, published Oct. 22, 1986 in the name of Duenk et al. Each of these patents are incorporated herein by reference. Another exemplary absorbent structure for use as the absorbent core 24 of the present invention is described in U.S. patent application entitled "Absorbent Core For Use In Catamenial Products", Ser. No. 07/734,405, filed Jul. 23, 1991, inventors Buenger et al.

A preferred embodiment of the absorbent core 24 comprises the laminate structure shown in FIG. 3. The laminate is comprised of a layer of superabsorbent polymeric (or absorbent gelling material) and one or more sheets or webs of cross-linked cellulosic fibers. Alternatively, the absorbent core 24, shown in FIGS. 2, 4, and 5, comprises a single sheet of cross-linked cellulosic fibers. Suitable cross-linked cellulosic fibers for the absorbent core 24 are of FIGS. 2–5 described in U.S. Pat. No. 4,888,093 issued to Cook et al. on Dec. 19, 1989; U.S. Pat. No. 4,822,543 issued to Dean et al. on Apr. 18, 1989; U.S. Pat. No. 4,889,595 issued to Schoggen et al. on Dec. 26, 1989; and U.S. Pat. No. 4,898,642 issued to Moore et al. on Feb. 6, 1990; U.S. Pat. No. 4,935,022 issued Jun. 19, 1990 to Lash et al.; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The cross-linked cellulosic fibers in the embodiment shown in FIG. 3 comprises a single sheet that wraps the layers of particles of absorbent gelling material 40. The sheet is wrapped so that it appears as having a "c" configuration when viewed from the end. The wrapped sheet forms an upper layer 41 and a lower layer 42. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other crosslinked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types. Once in hand, the curled cellulosic fibers are refined to provide the fibers used to prepare the preferred absorbent cores used in the practice of this invention.

Preferably, in order to provide sustained interfiber and intrafiber fluid transport in the fluid accepting and transporting layer 27 (which will be described in detail below), the absorbent core 24 has certain performance characteristics such as capillary suction, and fluid retention capacity. Preferably, the capillary suction of the absorbent core 24 should be greater than that of the capillary channel fibers 25 of the fluid accepting and transporting layer 27 and at least 6 cm of vertical wicking for the particular fluid to be handled by the absorbent article. Preferably, the fluid retention capacity of the absorbent core 24 is at least 5 g/g. The above performance characteristics are typically achieved in an absorbent core having a density of about 0.1 g/cc to about 0.2 g/cc.

C. Backsheet

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapors to escape from the absorbent core 24 (i.e., breathable) while still preventing exudates from passing through the backsheet 23.

D. Fluid Accepting and Transporting Layer

The fluid accepting and transporting layer 27 transports fluid from the point of insult to the fluid retaining material, i.e., absorbent core 24. Preferably, the fluid accepting and transporting layer 27 is a nonwoven comprised of capillary channels 25 having external capillary channels 29 on their outer surfaces. Capillary channel fibers 25 are fibers having channels 29 formed therein, preferably, on their exterior surfaces. FIGS. 6 to 9 show examples of some types of capillary channel fibers 25. Suitable capillary channel fibers are described below, and in the following patent applications which were filed on Jul. 23, 1991: U.S. patent application Ser. No. 07/734,404 filed in the names of Thompson et al.; U.S. patent application Ser. No. 07/734,392 filed in the names Thompson et al.; U.S. patent application Ser. No. 07/734,405 filed in the names of Buenger et al.; and U.S. patent application entitled "Spinneret Orifices and Filament Cross-Sections with Stabilizing Legs Therefrom", Ser. No. 07/918,174, filed Jul. 23, 1992, Inventors Phillips, et al. These patent applications may be referred to collectively as the "Capillary Channel Fiber" patent application. Suitable capillary channel fibers are also described in EPO Patent Application 0 391 814 published Oct. 10, 1990.

The nonwoven fluid accepting and transporting layer 27 can suitably be formed in any manner capable of forming nonwoven webs known to those skilled in the art. For example, the nonwoven layer 27 can be formed through a carding process, rando process, spunbond process, needlepunch process, or hydroentangling process. Preferably, the nonwoven layer 27 is formed from staple capillary channel fibers 25. The nonwoven fluid accepting and transporting layer 27 may comprise one or more layers of nonwoven webs superposed upon each other.

The nonwoven fluid accepting and transporting layer 27 preferably contains at least about 25% by weight, more preferably at least about 50% by weight of capillary channel fibers 25. While it is advantageous to maximize the amount of capillary channel fibers 25 in the nonwoven fluid accepting and transporting layer 27, there are advantages to having materials other than capillary channel fibers 25 in the layer 27. For example, binders, such as thermoplastic binder fibers or thermoplastic powders can be used to improve the tensile strength of the layer 27. Fibers that do not have capillary channels on their external surfaces, e.g., round cross-section fibers, can be incorporated into the fluid accepting and transporting layer 27. For example, a nonwoven structure comprising both capillary channel fibers and non-capillary channel fibers may be used as the fluid accepting and transporting layer 27. Other non-capillary channel materials can be selected to enhance the physical properties of the layer 27 provides these materials do not exceed 75% by weight of the fluid accepting and transporting layer 27.

The fluid accepting and transporting layer 27 utilizes both interfiber and most importantly intrafiber fluid transport to move fluid from the point of insult to the absorbent core 24. By providing enhanced intrafiber fluid transport a more effective use of the absorbent core 24 can be achieved. For example, by providing enhanced intrafiber fluid transport the fluid accepting and transporting layer 27 is able to withstand multiple insults of liquid and provide a clean and dry feel to the wearer.

While a variety of capillary channel fibers can be used herein, the following description discusses some preferred characteristics of the capillary channel fiber 25 that are incorporated into the absorbent articles of this invention.

(i) Fiber Morphology

The capillary channel fibers 25, as noted above, have capillary channels 29 on their outer surfaces. Capillary channel fibers comprise a polymer composition and have at least one capillary channel, wherein the capillary channel has a base and at least two walls extending from the base, typically (but not necessarily) along substantially the entire length of the base element, whereby the base element and walls define said capillary channel(s). Although the capillary channel fibers herein may have one capillary channel or a plurality of capillary channels, for convenience the plural form "channels" is used with the intent that it shall refer to a singular "channel" in fibers that can have either one such channel or a plurality of channels as fibers having more than one channel. The fibers are further characterized in that the cross-section of the capillary channels is open along a substantial length of the structure in the axial direction of the channels such that fluid can be received from outside of such channels. The capillary channel walls of the fibers of the present invent i on are substantially parallel to one another. Substantially parallel, as used herein in reference to cross-sectional parallelism of the walls, means that the alignment differential of adjacent capillary walls is by no than 40°, preferably by no more than about 30°, more preferably no more than about 20°. The procedure to determine wall parallelism is described below under the Test Methods heading. Although not intended to necessarily limit the invention, substantially parallel walls are believed to provide enhanced capillary fluid transport rates and capillary suction per unit weight of the fibers.

The capillary channel fibers of the present invention are characterized by having relatively thin walls and bases compared to the width of the capillary channels. In other words, the fibers of the present invention are also characterized by having relatively "slender" walls. The degree to which the walls and base of the capillary channel structures are slender can be characterized according to a "Slenderness Ratio," the calculation of which is described in the Test Methods sections below. The capillary channel fibers of the present invention preferably have a Slenderness Ratio of at least about 9, more preferably at least about 15.

The capillary channels have an average capillary channel width of from about 10 to 200 $\mu M$, more preferably from about 20 to 100 $\mu M$. In practice capillary channel fibers meeting the above specifications will have a denlet per filament of greater than about 5. To achieve rapid and economic transport of liquids, the capillary channel fibers will typically have Specific Capillary Volume (SCV) of at least about 1.0 cc/g, preferably at least about 2.0 cc/g and a Specific Capillary Surface Area (SCSA) of at least about 1000 $cm^2/g$, preferably at least about 2000 $cm^2/g$.

In general, SCV is a measure of the volumetric fluid capacity of the capillary channel fiber on a unit weight basis, and is therefore indicative of the economic efficiency of the capillary channel fibers. However, in order for a fiber with high SCV to also have high capillary suction (i.e., have excellent ability to wick fluids at a substantial volumetric rate, on a unit weight basis of the structure, via intrafiber capillary transport), the design of the fiber must provide for a relatively high degree of capillary channel surface area contact between the material of the solid structure and the liquid which is to be transported. This is because capillary suction is in part dependent upon the amount of interfacial contact area between the solid structure and fluid. The SCSA is a measure of the surface area, per unit weight of the fiber, of the capillary channels in the fibers herein available for contact with fluids. The combination of required SCV and SCSA as set forth herein is met by providing capillary channel fibers with efficient capillary channel design and with relatively thin capillary channel walls and/or channel bases.

The procedures to be used for determining Specific Capillary Volume, and Specific Capillary Surface Area are described below under the Test Methods heading.

The capillary channel fibers 25 used herein can be prepared from any convenient polymer which is non-swelling when wet. Polymers such as polyethylene, polypropylene, polyesters (preferred), and the like, are useful herein, so long as they are spinnable such that they can be formed with external capillary channels, as noted hereinabove. Conveniently, the polymers are melt-extrudable. Typically, the capillary channel fibers herein will be prepared from a synthetic polyethylene terephthalate polymer melt having an inherent viscosity ("IV") of from about 0.6 to about 0.9. (IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9, since this would allow the walls of the capillary channels to be thinner, yet sufficiently strong to avoid collapse under in-use pressure.

The depth:width ratio of the capillary channels herein is preferably about 2.0, but processing restrictions, as noted above, as well as for economic reasons, a depth:width ratio of greater than about 1.3 is typically employed. Typical and readily producible capillary channel fibers which are quite satisfactory for use herein thus have a depth-of-walls of about 38 microns and a width-between-walls of about 21 microns and a denier per filament of about 15. The walls, themselves, are typically about 3-15 microns thick. Although variations in these dimensions are acceptable, capillary channel fibers prepared from polyester and having these characteristics are quite effective for their intended purpose. Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

The capillary channels 29 can be of various shapes providing they meet the requirement noted above. Certain shapes can offer particular advantages in particular product applications. For example, "U"-shaped, "H"-shaped, and "C"-shaped with stabilizing legs depending therefrom. Furthermore, the basic shapes may be repeated or even branched to produce fibers containing multiple channels, but it will be appreciated that when more than about three repeating shapes are used, some additional stiffness may be noted in the fibers.

The manufacture of capillary channel fibers 25 of the type employed herein is described in EPO Application 391,814 and in co-pending U.S. continuation-in-part application entitled "Fibers Capable of Spontaneously Transporting Fluids", Ser. No. 07/736,261, filed Jul. 23, 1991, Inventors Phillips, Jones et al., Eastman Chemical Company; co-pending U.S. patent application entitled "Spinneret Orifices and Filament Cross-Sections with Stabilizing Legs Therefrom", Ser. No. 07/918,174, filed Jul. 23, 1992, Inventors Phillips, et al.; and in co-pending U.S. patent application entitled "Open Capillary Channel Structures, Improved Process for Making Capillary Channel Structures, and Extrusion Die for Use Therein", Ser. No. 07/482,446, filed Feb. 20, 1990, inventors Thompson and Krautter.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic.

The surface treatment of polymeric fibers involves processes which are well-known in the extensive fiber literature. In general, such processes involve treating the surface of the fibers with a "hydrophilizing agent", especially a surfactant. (Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactant useful in such processes include various nontoxic and antonic detersive surfactants of the general type known in the laundry literature. Hydrophlizing agents include wetting agents such as polyethylene glycol monolaurates (e.g., PEGOSPERSE 200 ML, a polyethylene glycol 200 monolaurate available from Lonza, Inc., Williamsport, Pa., U.S.A.), and ethoxylated oleyl alcohols (e.g., VOL-PO-3, available from Croda, Inc., New York, N.Y. U.S.A.). Other types of hydrophilizing agents and techniques can also be used, including those well known to those skilled in the fiber and textile arts for increasing wicking performance, improving soil release properties, etc. For example, suitable finishes include Eastman's LK5483, LK5563 and most preferably Eastman's LK5570, as well as the polymer available as MILEASE T, which is well-known in the detergency arts (see, for example, U.S. Pat. No. 4,132,680) as a fiber-coating ethylene terephthalate/polyethyleneglycol terephthalate soil release polymer which is available from ICI America. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

The objective is to provide a gradient of capillary suction between the topsheet 22 and underlying layer or layers of the articles herein, such that the liquid is drawn in the z-direction and away from the surface of the article and into its ultimate storage layer. Empirically, capillary suction is inversely related to the contact angle of the material and to the size of the openings, i.e., in a typical case, the openings in the topsheet will be larger than the intrafiber capillary channels, which, in turn, will be larger than the interfiber capillary openings in the fibrous storage core. The surface hydrophilicity of the components of each layer can also theoretically effect the capillary section gradient.

E. Fluid Flow Among the Various Layers

Initially fluid will impinge the topsheet 22 of the sanitary napkin 20 of FIGS. 2 and 4. Fluid will move through the topsheet 22 toward the nonwoven fluid accepting and transporting layer 27. Interfiber acceptance of the fluid occurs in nonwoven layer 27. As fluid contacts the capillary channel fibers 25 located within the nonwoven layer 27 intrafiber fluid transport occurs. In other words, the nonwoven layer 27 accepts fluid between the capillary channel fibers and transports the fluid via the intrafiber channels. In addition, some fluid will be transported between the capillary channel fibers. Fluid is then emptied from the intrafiber channels 29 of the nonwoven layer 27 by the high suction absorbent core 24. As fluid is emptied from the intrafiber channels they empty fluid from the interfiber spacings in nonwoven layer 27, thus readying the nonwoven layer 27 for a subsequent fluid insult.

When the nonwoven layer 27 is used as the topsheet as shown in FIGS. 3 and 5, fluid initially impinges the nonwoven layer 27 and is moved about the nonwoven layer 27 as discussed above.

F. Optional Retaining Means

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the national Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox El/O and BL30MG-A Silox 4P/O both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

G. Test Methods

The following procedures are useful for determination of parameters used to define and evaluate the capillary channel structures of this invention. Specific units may be suggested in connection with measurement and/or calculation of parameters described in the procedures. These units are provided for exemplary purposes only. Other units consistent with the intent and purpose of the procedures can be used.

(i) Specific Capillary Surface Area and Specific Capillary Volume Procedure

The procedure is used to determine Specific Capillary Surface Area (SCSA) and Specific Capillary Volume (SCV) of a capillary channel structure. The procedure is applied to a photomicrograph which shows a representative cross-section of the capillary channel structure. The cross-section of the structure is prepared for photomicrographing by embedding and microtoming techniques known to those skilled in the art. The following equations are used:

$$SCSA = \frac{\sum_{x=1}^{i} P_x}{\rho A_s} \quad (1)$$

$$SCV = \frac{\sum_{x=1}^{i} Av_x}{\rho A_s} \quad (2)$$

wherein:

$\rho$ = density of the solid (i.e., polymer);

$A_s$ = area of the cross-section of capillary channel solid perpendicular to the capillary channel axis which bounds those capillary channels within the scope of criteria (a) and (b), below;

$\sum_{x=1}^{i} P_x$ = the sum of the perimeters of the cross section of the solid forming each of the capillary channels, x, wherein each perimeter $P_x$ bounds the capillary channel and is within the theoretical closure provided by $C_x$;

$\sum_{x=1}^{i} Av_x$ = the sum of the void areas of the capillary channel fiber wherein each $Av_x$ is calculated as the area bounded by the perimeter of the solid forming the channel and by $C_x$;

and wherein i is the number of capillary channels in the fiber, x refers to specific capillary channels of a capillary channel fiber, and $C_x$ corresponds to that part of a circle which is convex toward the interior of the channel and which is of a selected diameter that closes each capillary channel, x, wherein the circle, $C_x$ is sized and positioned according to the following criteria:

(a) the circle, $C_x$, is tangent to both walls of the capillary channel, x, at the points where it meets the walls; and (b) for each capillary channel, x, the circle $C_x$ meeting (a) maximizes $Av_x$ for each such channel, x, subject to the limitations that:

(i) the lines tangential to the intersection of $C_x$ and the capillary channel walls intersect to form an angle of 120° or less; and (ii) $C_x$ can have a radius of no greater than about 0.025 cm with respect to the actual scale of the capillary channel structure (circle radius will be enlarged by the same magnification factor applied to the actual structure in the photomicrograph).

For capillary channels having multiple points of tangency with a circle of maximum radius, as provided above, the circle is positioned so as to maximize cross-sectional area (Av) of the channel. For capillary channel fibers having variation in cross-sectional size or shape, sufficient cross-sections can be evaluated to provide a representative weighted average SCV and/or SCSA.

The purpose of SCV and SCSA, as defined above, is to provide quantitative analysis of structures characterized by open capillary channels. It is conceivable that such structures can have solid portions, appendages, and the like, which do not otherwise contribute to the definition of the capillary channels in this procedure. The above criteria will exclude perimeter and void areas corresponding to such nonfunctional portions of the structure from the calculations. Also, the cross-sectional area of nonfunctional solid elements is not to be included in the calculation of $A_s$. Exclusion of such perimeters and cross-sectional area is exemplified in more detail below.

Figure 10:
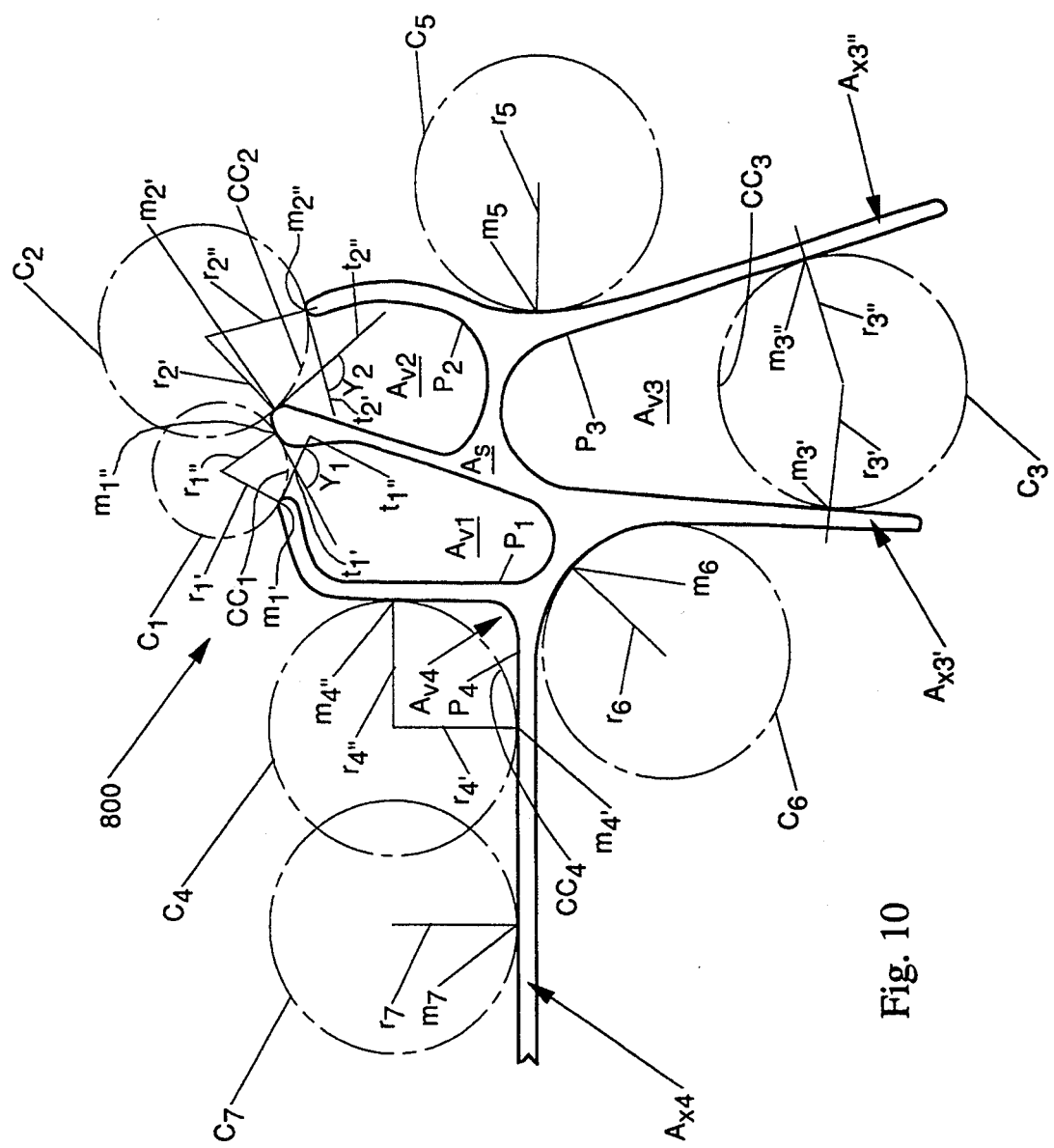
FIG. 10 is a cross-sectional view of a capillary channel fiber which exemplifies various aspects of procedures for calculating Specific Capillary Surface Area and Specific Capillary Volume.

FIG. 10 exemplifies a capillary channel structure fragment 800 and application of the SCV and SCSA procedure thereto. Shown is the fragment 800 of solid (i.e., polymer) having area $A_s$, capillary channel void areas $Av_1$, $Av_2$, $Av_3$, $Av_4$, with corresponding capillary channel perimeters $P_1$, $P_2$, $P_3$, $P_4$ and theoretical closure circles $C_1$, $C_2$, $C_3$, and $C_4$. Also shown are circles $C_5$, $C_6$, $C_7$. Radii $r_1'$, $r_1''$, $r_2'$, $r_2''$, $r_3'$, $r_3''$, $r_4'$, $r_4''$, $r_5$, $r_6$, $r_7$ are each perpendicular to the line tangent to the points of intersection $m_1'$, $m_1''$, $m_2'$, $m_2''$, $m_3'$, $m_3''$, $m_4'$, $m_4''$, $m_5$, $m_6$, $m_7$, respectively, between the corresponding circles, $C_1$, $C_2$, $C_3$, $C_4$, $C_5$, $C_6$, $C_7$ and the solid material of fragment 800.

The circles $C_1$, $C_2$, $C_3$, and $C_4$ are drawn so as to meet the above criteria. As can be seen circles $C_1$, and $C_2$ are limited in radius $r_1$, $r_2$ by angles $\gamma_1$, $\gamma_2$ which represent 120° angles of intersection between tangent lines $t_1'$, $t_1''$, and between $t_2'$, $t_2''$, respectively, $Av_1$, $Av_2$, $Av_3$, and $Av_4$ are the areas bounded by perimeters $P_1$, $P_2$, $P_3$, and $P_4$ and curves $cc_1$, $cc_2$, $cc_3$, and $cc_4$, respectively. Circles $C_3$ and $C_4$ represent the maximum size circle for capillary channels, wherein the angle of intersection of lines drawn tangent to the circle at points $m_3'$, $m_3''$, and at $m_4'$, $m_4''$, respectively, would be less than 120°. Thus, as represented in this exemplary figure, circles $C_3$ and $C_4$ would each have radius of 0.025 cm, after reduction for magnification effects. Perimeters are determined as the length of the solid boundary interior to the channels between the points of intersection between the circle and the solid for each channel. $C_5$, $C_6$, and $C_7$ represent circles of maximum radius applied to portions of the structure which do not qualify as capillary channels according to the criteria of this procedure. Hence P and Av for these circles would be zero, As can be seen, the area of the solid between $m_4'$ and $m_4''$ would be included within As since such solid corresponds to capillary channel walls bounding channels within the criteria for Av in the calculation of SCV and SCSA. Areas $A_{x3}'$ and $A_{x3}''$, which are bounded by linear extensions of the radii $r_3'$, $r_3''$, (said radii being perpendicular to the line of tangency between the circle $C_3$ and the walls of the channel), are not included in $A_s$. Likewise, radius $r_4''$ truncates area $A_{x4}$ from the calculation $A_s$ based upon extension of $r_4'$ of circle $C_4$.

(ii) Vertical Wicking Procedure

This procedure is used to determine the Vertical Wicking Height for absorbent cores and capillary channel fibers. In general, the purpose of the procedure is to visually observe and record the vertical position of fluid. The procedure is applied to strips of absorbent cores or single capillary channel fibers. The fluid to be used for evaluation of vertical wicking height should correspond to the fluid absorbed by the absorbent product during use. The test fluid can be dyed to facilitate measurements. Aqueous solutions can be dyed with 0.05% FD&C Blue #1 (hereinafter "Dyed Distilled Water"). Suitable FD&C Blue #1 dye is commercially available (e.g., from H. Kohnstamm & Co., Inc., N.Y., N.Y., U.S.A.). Blood-based fluids do not need to be dyed.

A closed bottom glass tube of approximately 25 cm height is provided. Sufficient test fluid is added to provide a depth of about 2.5 cm. A ruler marked in millimeters is attached to the outside of the tube. A rubber stopper is provided to close the top of the tube. The stopper has a centrally positioned hole to allow clamp means, for suspending a sample in place below the rubber stopper, to be inserted into the tube. The hole is sized such that the tweezers, or other clamp means as may be applicable, remain in a locked position when disposed within the rubber stopper hole. Tweezers can be sued as clamp means. Clamp means must fit into the hole in the rubber stopper so as to allow for adjustment in height of the sample. Alternatively, single capillary channel fibers can be attached to a rod such that they are held vertically from the top and bottom.

To initiate the procedure, a sample of an absorbent core or a capillary channel fiber is submerged and a timer is started. After 2 hours, the height of the liquid is measured.

(iii) Procedures for Slenderness Ratio and Capillary Channel Width

Slenderness Ratio (S) is determined according to the following procedure. The procedures are implemented based upon a photomicrograph of a representative microtomed cross-section of the capillary channel structure, as previously described. For capillary channel structures having variation in Slenderness Ratio in the axial direction of the capillary channels, sufficient cross-sections should be evaluated to provide a representative weighted average Slenderness Ratio.

The following equations are used:

$$S = L^2/4A_{st}$$

$$t_{ave} = 2A_{st}/L$$

wherein:
L = total solid perimeter of the cross-section of the structure; and
$A_{st}$ = total area of the cross-section of the solid forming the structure perpendicular to the capillary channel axis The foregoing equation for Slenderness Ratio treats the fiber under consideration as if it has one channel-forming wall therein. For channeled fibers having a functional portion wherein one or more channels are present, the formula for Slenderness Ratio (S) can be given as:

$$S = L^2/4A_{st}N$$

wherein:
L and $A_{st}$ are as hereinbefore defined; and
N = number of channel walls in the structure, said wall being those that have, on one or both sides, channels that are closable by straight closure chords.

Capillary channel width is the distance between the walls forming the capillary channels. Capillary channel width can be determined by reference to photomicrograph of fiber cross sections.

(iv) Procedure for Determining Wall Parallelism

Figure 11:
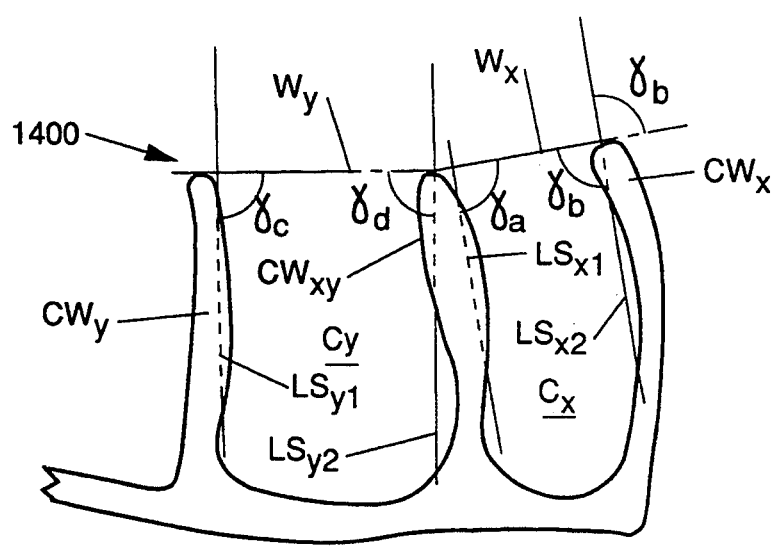
FIG. 11 is a cross-sectional view of a capillary channel fiber which exemplifies various aspects of procedures for calculating wall parallelism.

A representative cross-section of a capillary channel fiber is microtomed as previously described and a photomicrograph of the cross-section is prepared. Reference can be made to FIG. 11 which exemplifies various aspects of the procedure. For each capillary channel, of a capillary channel fiber, a straight channel closure chord tangentially contacting the capillary channel walls of the channel is drawn to close the channel while maximizing area within the closed channel. In practice, this can be done by simply placing a straight edge of a length in excess of the widest part of the channel, tangential to the distal portion of each of the walls forming the channel. The length of the chord is determined as the minimum distance between points of intersections between the chord and each of the two walls. Line segments $LS_{x1}$, $LS_{x2}$, each having a length, equal to 75% of the length of closure chord $W_x$, are located such that the ends of each such line segments $LS_{x1}$, $LS_{x2}$, contact the interior surfaces of channel walls $CW_x$, $CW_{xy}$ which serve as the boundary to the capillary channel. Similarly, the ends of line segments $LS_{y1}$, $LS_{y2}$ are 75% of the length of closure chord $W_y$ and contact the interior surfaces of channel walls $CW_y$, $CW_{xy}$, respectively. The line segments can cross the boundary of the channel walls at points intermediate to the ends of the line segments. If the line segments can be positioned such that the divergence angle between the line segments is from 0° to about 40°, the channel walls are said to be substantially parallel.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    (a) a fluid pervious topsheet, said topsheet comprising a nonwoven comprised of a plurality of hydrophilic capillary channel fibers capable of intrafiber and interfiber fluid acceptance and transport, said fibers having at least one capillary channel formed from a base and two substantially parallel walls extending from the base said topsheet having a predetermined capillary suction;
    (b) a fluid impervious backsheet joined to said topsheet; and
    (c) a high-suction absorbent core positioned between said topsheet and said backsheet, said core having an uppermost surface facing said topsheet and a lowermost surface facing said backsheet said absorbent core having a capillary suction greater than that of said topsheet.

2. The structure according to claim 1 wherein the capillary channel width of the capillary channel fibers of said nonwoven is from about 10 microns to about 200 microns.

3. The structure according to claim 1 wherein the denier of said capillary channel fibers of said nonwoven is greater than about 5.

4. The structure according to claim 1 wherein the divergence of the substantially parallel walls of the capillary channel fibers of said topsheet is less than about 40°.

5. The structure according to claim 1 wherein the slenderness ratio of said capillary channel fibers forming said topsheet is at least about 9.

6. The structure according to claim 1 wherein the capillary suction of said absorbent core is at least about 6 cm.

7. An absorbent article comprising:
    (a) a fluid pervious topsheet, said topsheet comprising a nonwoven comprised of a plurality of hydrophilic capillary channel fibers capable of intrafiber and interfiber fluid acceptance and transport, said topsheet having a predetermined capillary suction;
    (b) a fluid impervious backsheet joined to said topsheet; and
    (c) a high-suction absorbent core positioned between said topsheet and said backsheet, said core having an uppermost surface facing said topsheet and a lowermost surface facing said backsheet, said absorbent core having a capillary suction greater than that of said topsheet.

8. The structure according to claim 7, wherein the slenderness ratio of said capillary channel fibers forming said nonwoven is at least about 9.

9. The structure according to claim 7, wherein the capillary suction of said absorbent core is at least about 6 cm.

* * * * *